United States Patent [19]

Fowler

[11] Plant 5,220

[45] Apr. 17, 1984

[54] PEAR TREE ("AUTUMN RED")

[75] Inventor: Robert E. Fowler, Newcastle, Calif.

[73] Assignee: Fowler Nurseries, Inc., Newcastle, Calif.

[21] Appl. No.: 440,168

[22] Filed: Nov. 8, 1982

[51] Int. Cl.[3] ..... A01H 5/00
[52] U.S. Cl. ..... Plt./36
[58] Field of Search ..... Plt./36

*Primary Examiner*—James R. Feyrer
*Attorney, Agent, or Firm*—Roger B. Webster

[57] ABSTRACT

A pear tree which is of medium size and vigor, rapid growing, upright and tall with straight branches, vase-formed, hardy, foliated with medium size, ovate, taper-pointed, smooth, dark green leaves having a crenate to finely serrate margin, blooms with medium size, light pink to white flowers, and is a regular and productive to very productive bearer of large, uniform size, late ripening, juicy, sweet fleshed fruit; the fruit—in shape—being oblate and conical, ovate, oblique, symmetrical, and uniform, and the fruit having very waxy, highly glossy, deep red to purple-red skin, and white flesh.

1 Drawing Figure

BACKGROUND OF THE VARIETY

1. Field of the Invention

In the normal course of my agricultural activities, in the operation of an orchard and as an owner of a commercial fruit tree nursery, both located near Newcastle, Placer County, Calif., I am cognizant of the normal characteristics of many such trees, including pear trees. Hence, when unusual characteristics are observed by me in such a fruit tree, I am aware thereof. It is against this background that the present variety was originated.

2. Classification of the Variety

The present variety of pear tree is embraced by Class 36, Plants, of the U.S. Patent Office Manual of Classification.

3. Prior Varieties

Among existing varieties of pear trees which are known to me and mentioned herein are the Anjou, Bartlett, Comice, Sensation (all unpatented), and the Rosired (Rosired-Bartlett) (U.S. Plant Pat. No. 2,012).

ORIGIN OF THE VARIETY

The present variety of pear tree was originated by me as follows:

Seeds—selected at random from fruit of Anjou, Bartlett, Comice, Sensation, and Rosired pear trees in the aforementioned orchard—were planted and grown, in a large number, in nursery rows at the aforementioned fruit tree nursery. The resultant seedling pear trees were maintained under close, careful, and continuing observation, and, in maturity, one such seedling tree evidenced substantial promise as a commercial variety and was, therefore, selected by me for further testing and propagation.

ASEXUAL REPRODUCTION OF THE VARIETY

Asexual reproduction of the present variety of pear tree was successfully accomplished under my direction in said commercial nursery by budding; and such asexual reproductions, in maturity, ran true to the original seedling pear tree in all respects.

SUMMARY OF THE VARIETY

The present variety of pear tree is, characteristically, of medium size and vigor, rapid growing, upright and tall with straight branches, vase-formed, hardy, foliated with medium size, ovate, taper-pointed, smooth, dark green leaves having a crenate to finely serrate margin, blooms with medium size, light pink to white flowers, and is a regular and productive to very productive bearer of large, uniform size, late ripening, juicy, sweet fleshed fruit; the fruit—in shape—being oblate and conical, ovate, oblique, symmetrical, and uniform, and the fruit having very waxy, highly glossy, deep red to purple-red skin, and white flesh.

The present variety of pear tree is further characterized in the following respects:

While the growth habit of the tree is generally the same as the Rosired, the bark is more red to reddish purple in comparison to the gray-red or red-brown of the Rosired. At maturity, the trunk and branches have much the same coloring as the Bartlett.

The fruit is of a shape similar to the Rosired, but with some characteristics of the Comice, such as the slightly furrowed basin and the depth thereof.

The exterior color or blush of the fruit is a more true red than the maroon shade of the Rosired, and the fruit does not have the russeting and scab problems of the latter variety. At hard-ripe harvest, the fruit is a deep red to purple red, which lightens slightly when the fruit is eating ripe.

The fruit—which is juicy, sweet fleshed, of very good market quality, and possessed of substantial storage longevity—is in harvest for approximately one month, and which harvest extends about three weeks beyond the last picking of the Rosired.

The skin of the fruit is thicker than the Rosired, and has a very waxy surface which not only protects the fruit, but provides a high gloss especially when the skin is polished.

BRIEF DESCRIPTION OF THE DRAWING

The drawing is an illustration, by photographic reproduction in color, of a twig with leaves, and separate fruit of the variety; one fruit being half cut away to expose the flesh.

DESCRIPTION OF THE VARIETY

The botanical details of this new and distinct variety of pear tree—with color definitions (except those in common color terms) referenced to Maerz and Paul Dictionary of Color—are as follows:

Tree:
*Size.*—Medium.
*Vigor.*—Medium.
*Growth.*—Upright. Tall. Rapid.
*Form.*—Vase-formed.
*Hardiness.*—Hardy.
*Production.*—Productive to very productive.
*Bearing.*—Regular bearer.

Trunk:
*Size.*—Medium.
*Texture.*—Medium.

Branches:
*Size.*—Medium.
*Texture.*—Medium.
*Form.*—Straight.
*Color.*—Purple red to reddish brown.
*Lenticels.*—Number: Medium. Size: Medium.

Leaves:
*Size.*—Medium. Length: Medium — 5.2 cm. to 8.0 cm. Width: Medium — 1.8 cm. to 4.2 cm.
*Form.*—Ovate. Taper-pointed.
*Thickness.*—Medium.
*Color.*—Top side — Glossy dark green (23-C-8). Under Side — Lighter green (21-K-6).
*Texture.*—Smooth.
*Margin.*—Crenate. Finely serrate.
*Petiole.*—Length: Medium — 1 cm. to 2.5 cm. Thickness: Medium.

Flowers:
*Blooming period.*—Medium. With Bartlett.
*Size.*—Medium.
*Color.*—Very light pink to white.
*Fertility.*—Some fertile, others sterile.

Fruit:
*Ripening period.*—First picking: September 5th. Last picking: September 30th. Length of season: Approximately 1 month.
*Retention.*—Hangs well.
*Size.*—Large. Length — 3" to 3½". Width — 2½" to 3½". Uniform.
*Form.*—Oblate and conical. Ovate. Oblique. Symmetrical. Uniform.
*Stem.*—Short. Thick.
*Cavity.*—Obtuse. Medium depth. Medium breadth. Slightly russeted. Furrowed.
*Calyx.*—Partly open. Small to medium. Lobes: Separated at base. Short. Broad. Acute.
*Basin.*—Medium depth. Narrow width. Symmetrical. Slightly furrowed.

Skin:
*Thickness.*—Medium.
*Texture.*—Smooth. Very waxy. High glossy.
*Color.*—Ground color — green (19-L-2 to 19-L-7) substantially overspread with deep red (5-L-5) shading to purple red (7-L-6), with a medium number of medium size, submerged russet dots.

Flesh:
*Color.*—White (9-B-1).
*Texture.*—Firm. Crisp. Juicy.
*Flavor.*—Sweet.
*Eating quality.*—Very good.
*Core.*—Small size. Closed. Axile.
*Core lines.*—Meeting.
*Calyx tube.*—Length: Long. Width: Medium. Form: Conical.
*Seed.*—Small. Flat. Acuminate.

Use: Market. Home.
Keeping quality: Good — substantial storage longevity.
Resistance to insects and disease: Medium.
Shipping quality: Good.
Variance in botanical details: The pear tree and its fruit herein described may vary in slight detail due to climatic and soil conditions under which the variety may be grown; the present description being of the variety as grown in the Placer County area of California.

I claim:

1. A new and distinct variety of pear tree, substantially as illustrated and described, characterized by the bearing of late ripening fruit having a waxy, highly glossy, deep red to purple-red skin, and which fruit is in harvest for approximately one month, extending about three weeks beyond the last picking of the Rosired.

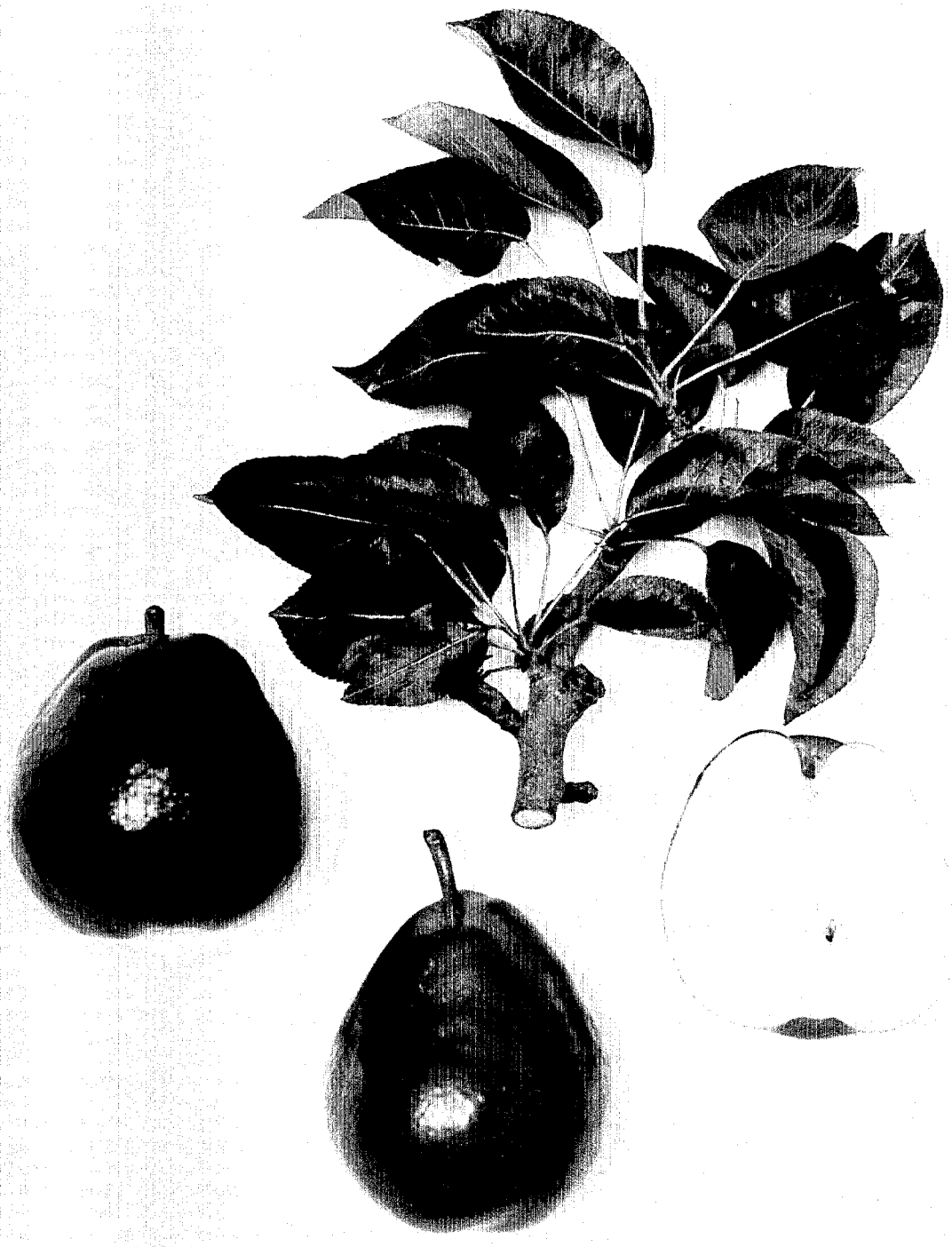

* * * * *